(12) United States Patent
Kajimoto et al.

(10) Patent No.: US 6,350,443 B1
(45) Date of Patent: Feb. 26, 2002

(54) METHOD OF TREATMENT FOR FELINE LEUKEMIA VIRUS INFECTIONS

(75) Inventors: Tsunesuke Kajimoto, Kanagawa; Tetsuya Shimoda, Okayama, both of (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 09/341,030

(22) PCT Filed: Oct. 30, 1997

(86) PCT No.: PCT/JP97/03962

§ 371 Date: Jul. 20, 1999

§ 102(e) Date: Jul. 20, 1999

(87) PCT Pub. No.: WO97/03421

PCT Pub. Date: Sep. 18, 1997

(51) Int. Cl.[7] ......................... A61K 38/21; A61K 38/00; C12P 21/04
(52) U.S. Cl. .................. 424/85.7; 424/85.4; 435/69.51; 514/2
(58) Field of Search ................. 424/85.4, 85.7; 435/69.51; 514/2

(56) References Cited

U.S. PATENT DOCUMENTS 5,508,291 A * 4/1996 Yanai et al. ................ 530/351

OTHER PUBLICATIONS

Rogers et al. Nature New Biology, 1972, vol. 237 (78), pp. 270–271.*

* cited by examiner

Primary Examiner—Yvonne Eyler
Assistant Examiner—Janet L. Andres
(74) Attorney, Agent, or Firm—Schnader Harrison Segal & Lewis LLP

(57) ABSTRACT

A method of treatment for feline leukemia virus infections by continuously administering a feline interferon preparation containing a feline interferon as a main component daily to a cat is disclosed. As a feline interferon, a feline ω (omega)-interferon is preferably used, and more particularly, a recombinant interferon is preferably used. A method of treatment using a therapeutic agent containing a feline ω-interferon as a main component in accordance with the present invention is a novel and superior method suitable for treating feline leukemia virus infections, and in particular, for treating neutropenia.

6 Claims, No Drawings

METHOD OF TREATMENT FOR FELINE LEUKEMIA VIRUS INFECTIONS

TECHNICAL FIELD

The present invention relates to a method of treatment for feline leukemia virus infections. Being an RNA tumor virus, which is a retrovirus, the feline leukemia virus is integrated into the DNA of its host cell. Due to infection by feline leukemia viruses, a great many types of hematopoietic diseases may develop. Specific hematopoietic diseases include, for example, immune system suppression, lymphatic leukemia, and sarcomas in lymphatic cells; agranulocytosis such as neutropenia, anemia, thrombocytopenia, and leukemia in bone marrow cells; and chronic stomatitis as complications with bacterial infection. In latter stages after infection with feline leukemia viruses, anemia and chronic stomatitis are often clinically observed, and the development of effective therapeutic agents and methods of treatment therefor has been eagerly awaited. However, although it will take many years before development of serious diseases, as described above, after infection with feline leukemia viruses, in the early stages after infection with these viruses, elevation of body temperature associated with a decrease in the number of neutrophils, decreases in vigor and appetite, and aggravation of other general clinical symptoms are often observed. Aggravation of neutropenia may sometimes result in death.

BACKGROUND ART

Conventionally, methods of treatment for feline leukemia virus infections mainly include symptomatic therapies using steroid hormones. Although human erythropoietin has been experimentally used as a remedy for anemia, satisfactory effects have not yet been achieved.

As causal therapies, use of synthetic anticancer agents which are human chemotherapeutics and use of a human $\alpha$ (alpha)-interferon have been proposed; however, the effects thereof are not satisfactory.

Hoover, et al., at Colorado State University, have attempted experimental therapies using AZT (3'-azido-3'-deoxythymidine) and a human $\alpha$-interferon for an immunodeficiency syndrome due to a feline leukemia virus, and have reported a reduction effect on the p27 antigen, which is an antigen of the feline leukemia virus. However, they have also admitted that the effect diminishes because antibodies are produced against the human interferon, which is a foreign protein to cats, after continued administration of the human $\alpha$-interferon, and thus, there is a problem in this as a method of treatment for feline leukemia virus infections. [Zeidner, N. S., Myles, M. H., Mathiason, D. C., Dreit, M. J., Mullins, J. I. and Hoover, E. A.; 1990a; Alpha Interferon (2b) in combination with zidovudine for the treatment of presymptomatic feline leukemia virus-induced immunodeficiency syndrome; Antimicrob. Agents Chemother.; 34: 1749–1749.]

Tompkins, et al., at North Carolina State University, have reported that, as treatment for feline leukemia viral lymphoma development, DEC (diethylcarbamazine) and AZT are effective at reducing p27 antigen and at prolonging life. However, neither was effective for neutropenia. [Nelson, P., Sellon, R., Novotoney, C., Devera, C., Davidian, M., English, R., Tompkins, M., and Tompkins, W.; 1995; Vet. Immunol. Immunopathol.; 46,181–194]

Cummins, et al., have orally administered to cats infected with feline leukemia viruses a low dose of a human $\alpha$-interferon and have reported that it is effective at prolonging life, although there is no effect on virus antigens. Although this therapy was later globally investigated as a method for treating human AIDS, the use thereof has not been implemented. [Weiss, R. C., Cummins, J. M., and Richards, A. B.; 1991; JAVMA; 199,1477–1481]

In various feline leukemia virus infections, since, in many cases, immunocompetence of cats is believed to be degraded, heavy use of steroid hormones, which are immunosuppressant agents, is not desirable, and side effects thereof often present a problem.

In addition, use of synthetic anticancer agents which are human chemotherapeutics and the oral administration of a small amount of a human $\alpha$-interferon are not adequately effective, and in the former synthetic anticancer agents, in particular, side effects are a problem.

As a feline interferon, a recombinant feline $\omega$-interferon preparation has already been approved as a therapeutic agent for feline calicivirus infection, and has been commercially available under the trade name "INTERCAT" since February 1994. The present inventors have achieved the present invention as a result of the investigation of a method of treatment for feline leukemia virus infection using the recombinant feline $\omega$-interferon.

Currently interferons are known to be of the following types: alpha ($\alpha$), beta ($\beta$), gamma ($\gamma$), omega ($\omega$), and tau ($\tau$). Although use of three types $\alpha$, $\beta$, and $\gamma$ has been implemented with respect to human interferons, in feline interferons, use of the $\omega$-type only has been implemented. "INTERCAT" is a recombinant feline $\omega$-interferon preparation, and is an injectable preparation produced by a method including the steps of infecting a silkworm with a baculovirus having recombinant feline $\omega$-interferon genes; extracting and purifying products of the body thereof; adding thereto gelatin and D-sorbitol as stabilizers and vehicles; and freeze-drying. The recombinant feline $\omega$-interferon is a glycoprotein having a molecular weight of approximately 25,000, and the protein portion thereof has the amino acid sequence as shown in the sequence listing (SEQ ID:1).

The feline $\omega$-interferon may be produced by other methods, in addition to the use of silkworms. For example, it may be produced by a transient expression method using zooblasts such as simian COS cells, or by gene recombination techniques using CHO cells of Chinese hamsters, E. coli, yeast, transgenic animals, or the like.

With respect to the administration/dosage of INTERCAT which has been approved as a therapeutic agent for feline calicivirus infectious diseases, 2.5 to 5 MU/kg of the feline interferon is required to be administered intravenously once a day for three times every other day. Herein, an MU (megaunit) represents a titer used as a measure of the antiviral activity of the interferon, and is equal to one million units. Although treatment for feline leukemia virus infections, in particular, neutropenia, was attempted by administering INTERCAT every other day with the same administration/dosage as those for the approved therapeutic agent for feline calicivirus infections, the anticipated effects were not obtained. Therefore, by changing the administration/dosage, further investigations were carried out.

DISCLOSURE OF INVENTION

It is an object of the present invention to provide a novel and superior method of treatment which is suitable for feline leukemia virus infections, and in particular, for neutropenia.

In order to achieve the object described above, the present inventors investigated and discovered a method of treatment for feline leukemia virus infections by administering to cats by injection a therapeutic agent containing a feline ω (omega)-interferon, leading to the present invention.

That is, the object of the present invention has been achieved with industrial advantages by the present invention comprising the following aspects.

(1) A method of treatment for feline leukemia virus infections including continuous daily administration of a feline interferon preparation containing a feline interferon as a main component to a cat.

(2) A method of treatment for feline leukemia virus infections according to (1), wherein the feline interferon is a feline ω (omega)-interferon.

(3) A method of treatment for feline leukemia virus infections according to (2), wherein the feline ω-interferon is a recombinant interferon.

(4) A method of treatment for feline leukemia virus infections according to (3), wherein the feline ω-interferon is an interferon having an amino acid sequence shown in the sequence number 1 in which a sugar chain is connected.

(5) A method of treatment for feline leukemia virus infections according to any one of (1) to (4), wherein the injection is a subcutaneous injection.

(6) A method of treatment for feline leukemia virus infections according to any one of (1) to (5), wherein the treatment is provided for neutropenia due to infection with a feline leukemia virus.

(7) A method of treatment for feline leukemia virus infections according to any one of (1) to (6), wherein the feline ω-interferon is administered in a dose of 0.5 MU/kg to 2.0 MU/kg per cat weight, at least once a day, for at least three consecutive days.

BEST MODE FOR CARRYING OUT THE INVENTION

A feline interferon used in the present invention is preferably a feline ω-interferon, and may be any one of a natural interferon, a chemically synthesized interferon, and an interferon produced by a genetic recombination technique.

Specifically, a feline ω-interferon commercially available under the trade name "INTERCAT" (produced by Toray Industries, Inc.) may be used, which is produced by a genetic recombination technique.

"INTERCAT" has been approved and used as a therapeutic agent for feline calicivirus infections, and has an interferon as a main component. In the interferon, a sugar chain-is connected to-an amino acid sequence containing 170 amino acids shown in SEQ ID:1 and the interferon is obtained by infecting silkworm larvae with a recombinant baculovirus as an insect virus having recombinant feline ω-interferon genes and by extracting, separating, and purifying products in the silkworm fluid.

However, a feline ω-interferon in the present invention is not necessarily limited to the recombinant feline interferon described above.

In cats having feline leukemia virus infections, whose infections have been confirmed by the fact that the virus examinations of the blood of the cats reveal that feline leukemia virus antigens (FeLV antigens) are positive, in the early stage of the feline leukemia virus infection, neutropenia is particularly observed. An effective method for treating neutropenia using a therapeutic agent containing a feline ω-interferon has been discovered. Neutropenia is confirmed by testing the blood of cats. In feline leukemia virus infections, in addition to a decrease in the number of neutrophils, a decrease in the number of thrombocytes is often observed.

A method of treatment discovered by the present inventors includes daily injections into a cat, at least once a day, a therapeutic agent containing a feline ω-interferon. The feline interferon is administered in a dose of 0.5 MU/kg to 2.0 MU/kg per cat weight.

The number of administrations is practically once a day. Although administration may be performed more than once a day, administration at least once a day is preferable. Instead of every other day, administration every day is preferable, and daily-administration for at least three consecutive days is further preferable. If possible, daily administration for at least five consecutive days is effective. When administration must be discontinued after administering for at least three consecutive days due to the pet owner's circumstances or the like, at an early stage after the discontinuance, another daily administration for at least three consecutive days is preferably performed.

Although a dose of less than 0.5 MU/kg may be administered, as the dose is decreased from 0.5 MU/kg, the therapeutic efficacy is decreased. On the other hand, a high dose of more than 2.0 MU/kg merely increases the treatment cost, and in many cases does not greatly increase efficacy.

With respect to the route of administration by injection, subcutaneous injections are most preferably used. Although intravenous injections are more difficult than subcutaneous injections because of difficulties in locating blood vessels, intravenous administration may be used. Although intramuscular injections are not preferable because of induced pain, in terms of efficacy, intramuscular injections may be used.

Many cats having feline leukemia virus infections are brought to veterinarians because of fever, loss of vigor, anorexia, and the like, and blood tests indicate neutropenia. In such a case, a method of treatment using a therapeutic agent containing a feline ω-interferon in accordance with the present invention is preferably used. As supportive therapies, transfusions and antibiotics are also preferably administered.

Consequently, alleviation of fever, revivification, and recovery of appetite are observed, and blood tests reveal that the number of neutrophils, which had decreased, rapidly increased, and sometimes that the number of thrombocytes increased at the same time.

EXAMPLES

Although examples in the present invention will be described below, it is to be understood that the invention is not limited to these examples. Blood cell count is represented in units of microliters ($/\mu l$).

Example 1

A recombinant feline ω-interferon preparation (Trade Name: INTERCAT) was administered to a 6-month-old crossbred male cat which was observed to have neutropenia due to a feline leukemia virus infection. On the first day of examination, the cat weighed 3.7 kg and had a body temperature of 39.5° C., had completely lost its appetite, lost vigor, and was observed to have gingivitis and purulent rhinorrhea. Blood test results were as follows: PCV 41%, WBC 8,800, neutrophil 484, lymphocyte 3,256, monocyte 5,016, eosinophil 44, and thrombocyte 200,000. In the virus test, an FeLV antigen was detectable and an FIV antibody was not detectable.

The INTERCAT was dissolved in a physiological saline solution, and was subcutaneously injected, at a dose of 4

MU/day, for three days. The dose was 1.08 MU/kg per cat weight. A transfusion (lactate Ringer's solution and glucose) was injected by intravenous drip infusion at a dose of 500 ml/day, and an antibiotic (cephalexin) was intravenously injected at a dose of 150 mg twice a day.

On the third day, the cat regained its appetite and had a body temperature of 38.2° C. and a weight of 3.6 kg. Blood test results were as follows: PCV 40%, WBC 10,100, neutrophil 2,121, lymphocyte 5,555, monocyte 2,121, eosinophil 303, and thrombocyte 100,000. Significant increases in the number of neutrophils and lymphocytes were observed, alleviation of fever and improved general condition were observed, and gingivitis and purulent rhinorrhea were cured.

However, on the seventh day, the cat had a body temperature of 40.2° C. and had lost appetite and vigor, and discharges from the eyes and lingual erosion were observed. Blood test results were as follows: PCV 29%, WBC 8,500, neutrophil 1,530, lymphocyte 2,550, monocyte 4,420, eosinophil 0, and thrombocyte 200,000.

The INTERCAT was subcutaneously injected 4 times at a dose of 4 MU/day, every other day. As combined remedies, on the day when the INTERCAT was administered, a transfusion (lactate Ringer's solution and glucose) was injected by intravenous drip infusion at a dose of 500 ml/day, and an antibiotic (cephalexin) was intravenously injected twice a day at a dose of 150 mg.

On the 12th day, body temperature had decreased to 38.3° C., and appetite and vigor were regained. Blood test results were as follows: PCV 32%, WBC 17,200, neutrophil 8,084, lymphocyte 6,880, monocyte 2,236, eosinophil 0, and thrombocyte 200,000.

On the 19th day, although no abnormalities were observed when the cat was examined, as a precaution, a dose of 4 MU of INTERCAT was subcutaneously injected.

After one month, it was recognized that the FeLV antigen level had become undetectable. The cat weighed 4.05 kg. Blood test results were as follows: PCV 39%, WBC 19,300, neutrophil 3,492, lymphocyte 8,299, monocyte 1,158, eosinophil 1,351, and thrombocyte 200,000.

After one year, the FeLV was also undetectable. The cat weighed 4.5 kg. Blood test results were as follows: PCV 42%, WBC 7,100, neutrophil 3,763, lymphocyte 2,982, monocyte 71, eosinophil 284, and thrombocyte 200,000.

Example 2

A recombinant feline ω-interferon preparation (Trade Name: INTERCAT) was administered to a one-and-a-half-year-old crossbred male cat which was observed to have neutropenia due to a feline leukemia virus infection. On the first day of examination, the cat weighed 2.9 kg and had a body temperature of 37.0° C., that was low, and had completely lost its appetite. Vomiting, diarrhea, and dehydration were observed. It was confirmed that the cat did not have a Parvovirus infectious disease. Blood test results were as follows: PVC 49%, WBC 3,600, neutrophil 1,476, lymphocyte 1,440, monocyte 576, eosinophil 108, and thrombocyte 30,000. In the virus test, an FeLV antigen was detectable, an FIV antibody was not detectable, and a Parvovirus antigen was not detectable.

The INTERCAT was dissolved in a physiological saline solution and was subcutaneously injected at a dose of 3 MU/day for four days. The dose was 1.03 MU/kg per cat weight. A transfusion (lactate Ringer's solution and glucose) was injected by intravenous drip infusion at a dose of 500 ml/day, and an antibiotic (cephalexin) was intravenously injected at a dose of 100 mg twice a day.

On the third day, the cat had a body temperature of 39.2° C., had no appetite, and had continuing diarrhea. Blood test results were as follows: PCV 34%, WBC 20,400, neutrophil 12,700, lymphocyte 3,700, monocyte 1,900, eosinophil 660, and thrombocyte 50,000. On the eighth day, the body temperature had decreased to 38.8° C. and appetite had slightly improved. The cat weighed 2.6 kg and had slight continuing diarrhea. Blood test results were as follows: PVC 22%, WBC 62,900, neutrophil 53,000, lymphocyte 2,300, monocyte 6,500, eosinophil 1,050, and thrombocyte 200,000.

The significant recovery of neutrophils was observed, and alleviation of fever and improved general condition were observed.

After one month and again after 10 months, no abnormalities were observed, and thus the therapeutic efficacy of the INTERCAT was recognized.

Example 3

A recombinant feline o-interferon preparation (Trade Name: INTERCAT) was administered to a 3-year-old crossbred male cat which was observed to have neutropenia due to a feline leukemia virus infection. On the first day of examination, the cat had a weight of 4.4 kg and a body temperature of 41.2° C., and a complete loss of appetite; abscesses and vomiting were observed. Blood test results were as follows: PVC 38%, WBC 900, neutrophil 0, lymphocyte 900, monocyte 0, eosinophil 0, and thrombocyte 30,000. In the virus test, an FeLV antigen was detectable, an FIV antibody was not detectable, and a Parvovirus antigen was not detectable.

The INTERCAT was dissolved in a physiological saline solution, and was subcutaneously injected at a dose of 5 MU/day for seven days. The dose was 1.14 MU/kg per cat weight. A transfusion (lactate Ringer's solution and glucose) was injected by intravenous drip infusion at a dose of 500 ml/day, and an antibiotic (cephalexin) was intravenously injected at a dose of 150 mg twice a day.

On the fifth day, the cat had a body temperature of 40.4° C., had no appetite, and had continuing diarrhea. Blood test results were as follows: PCV 32%, WBC 10,000, neutrophil 7,300, lymphocyte 2,300, monocyte 200, eosinophil 200, and thrombocyte 150,000. On the seventh day, the body temperature had decreased to 38.4° C. and appetite had recovered. Blood test results were as follows: PCV 34%, WBC 16,400, neutrophil 15,000, lymphocyte 1,400, monocyte 0, eosinophil 0, and thrombocyte 200,000.

Significant recovery of neutrophils was observed, and abatement of fever and improved general condition were observed.

The FeLV antigen was detectable.

Example 4

A recombinant feline o-interferon preparation (Trade Name: INTERCAT) was administered to a 5-year-old crossbred female cat (sterilized), which was observed to have neutropenia due to a feline leukemia virus infection. On the first day of examination, the cat had a weight of 3.25 kg and a body temperature of 40.7° C., and a complete loss of appetite, a loss of vigor, and pneumonia were observed. Blood test results were as follows: PCV 37%, WBC 1,100, neutrophil 22, lymphocyte 836, monocyte 132, eosinophil 88, and thrombocyte 30,000. In the virus test, both an FeLV antigen and an FIV antibody were detected.

The INTERCAT was dissolved in a physiological saline solution, and was subcutaneously injected at a dose of 5 MU/day for four days. The dose was 1.54 MU/kg per cat weight. A transfusion (lactate Ringer's solution and glucose) was injected by intravenous drip infusion at a dose of 500 ml/day, and an antibiotic (cephalexin) was intravenously injected at a dose of 100 mg twice a day.

Blood test results on the third day were as follows: PCV 36%, WBC 8,400, neutrophil 3,864, lymphocyte 3,444, monocyte 840, eosinophil 168, and thrombocyte 30,000. On the fifth day, the body temperature had decreased to 38.6° C., and the blood examination results were as follows: PCV 32%, WBC 7,300, neutrophil 4,088, lymphocyte 2,920, monocyte 292, eosinophil 0, and thrombocyte 60,000.

On the 10th day, the body temperature was 38.5° C., appetite and vigor had recovered, and pneumonia was also cured. The cat had a weight of 3.3 kg. Blood test results were as follows: PCV 31%, WBC 11,468, neutrophil 7,568, lymphocyte 3,325, monocyte 573, eosinophil 0, and thrombocyte 100,000.

On the 18th day, in the virus test, the FeLV antigen was not detected, the FIV antibody also was not detected. After one year, both the FeLV antigen and the FIV antibody were not detected.

Example 5

A recombinant feline ω-interferon preparation (Trade Name: INTERCAT) was administered to a 6-month-old crossbred female cat, which was observed to have neutropenia due to a feline leukemia virus infection. On the first day of examination, the cat had a weight of 2.2 kg and a body temperature of 41.5° C., and a complete loss of appetite, a loss of vigor, rhinorrhea, slaver, and dacryorrhea were observed. Blood test results were as follows: PCV 32%, WBC 4,400, neutrophil 2,885, lymphocyte 961, monocyte 732, eosinophil 0, and thrombocyte 100,000. In the virus test, an FeLV antigen was detected, an FIV antibody was not detected, and a Parvovirus antigen was not detected.

The INTERCAT was dissolved in a physiological saline solution, and was subcutaneously injected at a dose of 3 MU/day for five days. The dose was 1.36 MU/kg per cat weight. A transfusion (lactate Ringer's solution and glucose) was injected by intravenous drip infusion at a dose of 500 ml/day, and an antibiotic (cephalexin) was intravenously injected at a dose of 150 mg twice a day.

On the fifth day, the cat had a body temperature of 38.9° C., had an appetite, and rhinorrhea, slaver, and dacryorrhea were alleviated. Blood test results were as follows: PCV 26%, WBC 8,500, neutrophil 6,855, lymphocyte 1,020, monocyte 425, eosinophil 170, and thrombocyte 200,000. On the 13th day, aggravation occurred again. The body temperature was 40.2° C., anorexia was observed, and rhinorrhea, slaver, and dacryorrhea were aggravated. Blood test results were as follows: PCV 28%, WBC 7,000, neutrophil 840, lymphocyte 4,340, monocyte 1,680, eosinophil 140, and thrombocyte 200,000.

The INTERCAT was again subcutaneously injected at a dose of 3 MU/day for four days. The transfusion or antibiotic was not administered.

On the 17th day, the body temperature was 38.50° C., and appetite and vigor had recovered. Blood test results were as follows: PCV 24%, WBC 19,100, neutrophil 10,186, lymphocyte 7,003, monocyte 1,782, eosinophil 127, and thrombocyte 200,000.

Example 6

A recombinant feline ω-interferon preparation (Trade Name: INTERCAT) was administered to a 2-year-old crossbred male cat, which was observed to have neutropenia due to a feline leukemia virus infection. On the first day of examination, the cat had a weight of 3.9 kg and a body temperature of 40.4° C., and lymphatic swelling was observed. The cat had an appetite and vigor. Blood test results were as follows: PCV 22%, WBC 5,800, neutrophil 696, lymphocyte 4,698, monocyte 116, eosinophil 290, and thrombocyte 200,000. In the virus test, an FeLV antigen was detected and an FIV antibody was not detected.

After 5 days, although appetite and vigor were observed, the body temperature was 39.2° C., and blood test results were as follows: PCV 22%, WBC 5,800, neutrophil 131, lymphocyte 4,963, monocyte 219, eosinophil 483, and thrombocyte 200,000.

The INTERCAT was dissolved in a physiological saline solution and was subcutaneously injected at a dose of 4 MU/day for six days. The dose was 1.03 MU/kg per cat weight. A transfusion (lactate Ringer's solution and glucose) was injected by intravenous drip infusion at a dose of 500 ml/day, and an antibiotic (cephalexin) was intravenously injected at a dose of 100 mg twice a day.

On the second day after the administration of the INTERCAT, the body temperature was 39.5° C., and blood test results were as follows: PCV 24%, WBC 4,200, neutrophil 400, lymphocyte 3,400, monocyte 200, eosinophil 200, and thrombocyte 200,000.

On the fourth day, the body temperature was 38.7° C., and blood test results were as follows: PCV 23%, WBC 5,000, neutrophil 1,150, lymphocyte 3,100, monocyte 450, eosinophil 200, and thrombocyte 200,000. On the seventh day, the body temperature was 38.9° C., and blood test results were as follows: PCV 18%, WBC 6,100, neutrophil 1,769, lymphocyte 3,050, monocyte 1,220, eosinophil 61, and thrombocyte 200,000.

In this example, significant recovery of neutrophils was not observed, and abatement of fever and improved general condition were observed.

INDUSTRIAL APPLICABILITY

A method of treatment using a therapeutic agent containing a feline ω-interferon as a main component in accordance with the present invention is a novel and superior method suitable for treating feline leukemia virus infections, and in particular, for treating neutropenia. Using the method of treatment by subcutaneously injecting the feline ω-interferon preparation at least once a day for at least three consecutive days, the number of neutrophils, which has decreased, are increased, improvement in clinical symptoms such as alleviation of fever, recovery of vigor, and recovery of appetite are observed, and significant therapeutic efficacy can be achieved. At the same time, the number of thrombocytes, which has decreased, is sometimes increased. Additionally, no side effects are seen in accordance with the method of treatment in the present invention.

What is claimed is:

1. A method of treatment for feline leukemia virus infections comprising daily administration of a feline interferon preparation containing feline ω (omega)-interferon as a main component to a cat.

2. The method of treatment for feline leukemia virus infections according to claim 1, wherein the feline ω-interferon is a recombinant interferon.

3. The method of treatment for feline leukemia virus infections according to claim 2, wherein the feline ω-interferon is an interferon having an amino acid sequence of SEQ ID: 1, wherein said interferon is glycosylated.

4. The method of treatment for feline leukemia virus infections according to claim 1, wherein administration is by subcutaneous injection.

5. The method of treatment for feline leukemia virus infections according to claims 1, wherein said treatment is provided for neutropenia due to infection with a feline leukemia virus.

6. The method of treatment for feline leukemia virus infections according to claim 1, wherein said feline ω-interferon is administered in a dose of 0.5 MU/kg to 2.0 MU/kg per feline weight at least once a day for at least three consecutive days.

* * * * *

SEQUENCE LISTING

<160> NUMBER OF SEQ ID NOS: 1

<210> SEQ ID NO 1
<211> LENGTH: 170
<212> TYPE: PRT
<213> ORGANISM: Felis sp.

<400> SEQUENCE: 1

```
Cys Asp Leu Pro Gln Thr His Gly Leu Leu Asn Arg Arg Ala Leu Thr
 1               5                  10                  15

Leu Leu Gly Gln Met Arg Arg Leu Pro Ala Ser Ser Cys Gln Lys Asp
            20                  25                  30

Arg Asn Asp Phe Ala Phe Pro Gln Asp Val Phe Gly Gly Asp Gln Ser
        35                  40                  45

His Lys Ala Gln Ala Leu Ser Val Val His Val Thr Asn Gln Lys Ile
    50                  55                  60

Phe His Phe Phe Cys Thr Glu Ala Ser Ser Ala Ala Trp Asn Thr
65                  70                  75                  80

Thr Leu Leu Glu Glu Phe Cys Thr Gly Leu Asp Arg Gln Leu Thr Arg
            85                  90                  95

Leu Glu Ala Cys Val Leu Gln Glu Val Glu Glu Gly Glu Ala Pro Leu
            100                 105                 110

Thr Asn Glu Asp Ile His Pro Glu Asp Ser Ile Leu Arg Asn Tyr Phe
            115                 120                 125

Gln Arg Leu Ser Leu Tyr Leu Gln Glu Lys Lys Tyr Ser Pro Cys Ala
        130                 135                 140

Trp Glu Ile Val Arg Ala Glu Ile Met Arg Ser Leu Tyr Tyr Ser Ser
145                 150                 155                 160

Thr Ala Leu Gln Lys Arg Leu Arg Ser Glu
                165                 170
```